United States Patent [19]  [11] 4,307,258
Sollott  [45] Dec. 22, 1981

[54] HNS FROM 2,4,6-TRINITROBENZYL CHLORIDE AND NITROGENOUS BASES

[75] Inventor: Gilbert P. Sollott, Plymouth Meeting, Pa.

[73] Assignee: The United States of America as represented by the Secretary of the Army, Washington, D.C.

[21] Appl. No.: 165,429

[22] Filed: Jul. 2, 1980

[51] Int. Cl.$^3$ .............................................. C07C 79/10
[52] U.S. Cl. .................................................... 568/931
[58] Field of Search ........................................ 568/931

[56] References Cited

U.S. PATENT DOCUMENTS

| | | | |
|---|---|---|---|
| 3,505,413 | 4/1970 | Shipp | 568/931 |
| 4,085,152 | 4/1978 | Salter et al. | 568/931 |
| 4,221,745 | 9/1980 | Gilbert | 568/931 |
| 4,221,746 | 9/1980 | Gilbert | 568/931 |
| 4,238,420 | 12/1980 | Bird et al. | 568/931 |
| 4,238,421 | 12/1980 | Bird et al. | 568/931 |
| 4,243,614 | 1/1981 | Gilbert | 568/931 |
| 4,255,358 | 3/1981 | Jones et al. | 568/931 |
| 4,270,012 | 5/1981 | Gilbert | 568/931 |

OTHER PUBLICATIONS

Shipp, K. G., et al., J. Org. Chem., vol. 31, pp. 857–861, (Mar. 1966).

*Primary Examiner*—Teddy S. Gron
*Attorney, Agent, or Firm*—Nathan Edelberg; Robert P. Gibson; A. Victor Erkkila

[57] ABSTRACT

2,4,6-trinitrobenzyl chloride is converted to HNS (2,2',4,4',-6,6'-hexanitrostilbene) by reaction with hydroxide ion supplied by aqueous amines and ammonia. The present method increases the yield of HNS substantially over that obtainable by conventional reaction with sodium hydroxide.

12 Claims, No Drawings

HNS FROM 2,4,6-TRINITROBENZYL CHLORIDE AND NITROGENOUS BASES

GOVERNMENTAL INTEREST

The invention described herein may be manufactured, used and licensed by or for the Government for Governmental purposes without the payment to me of any royalties thereon.

BACKGROUND OF THE INVENTION

This invention relates to the production of 2,2',4,4',6,6'-hexanitrostilbene.

2,2',4,4',6,6'-hexanitrostilbene (HNS) is a well known thermally stable explosive. U.S. Pat. No. 3,505,413 describes the preparation of HNS by the reaction of 2,4,6-trinitrotoluene (TNT) with sodium hypochlorite. The yield of HNS obtained by this method ranged up to about 35% after purification and washing. British patent application No. 250,1/76 discloses the preparation of HNS from TNT by a process which is similar to that disclosed in the '413 patent, but which differs by the addition of a nitrogenous base to the reaction mixture at least 0.5 minutes after the start of the reaction. The British Applicants state that the presence of the nitrogenous base increases the yield of HNS to between 45 and 50% of theoretical, by contrast with the yields of the prior art process which ranged from 30 to 35%.

Earlier investigations of the reaction of TNT to form HNS, by Shipp and Kaplan, reported in the Journal of Organic Chemistry, Volume 31, Page 857 (1966), dealt separately with the conversion of 2,4,6-trinitrobenzyl chloride to HNS by reaction with aqueous sodium hydroxide which is present in the sodium hypochlorite solution during its reaction with TNT. For example, with a mole ratio of 1:1.0 of the benzyl chloride to hydroxide, the crude HNS yield was found to be 50%. Likewise, they found that the oxidation of TNT with the hypochlorite resulted in a 42% crude yield of HNS. The crude yields mentioned herein, are significant in that the actual yields of HNS are reduced after the crude products are washed with acetone to remove coprecipitated by-product impurities. Therefore, one of the objects of researchers in the art has been to increase the yield of purified HNS available.

Shipp and Kaplan, in the above-mentioned article isolated the benzyl chloride as an intermediate in the conversion of TNT to HNS. The British Applicants dealt directly with the conversion of TNT, and did not deal with the isolated benzyl chloride. Moreover, the method of the British application contemplates the inclusion of the nitrogenous base together with the excess hypochlorite which is alkaline because of the presence of excess sodium hydroxide.

SUMMARY OF THE INVENTION

In accordance with the present invention, 2,2',4,4',6,6'-hexanitrostilbene (HNS) may be prepared from 2,4,6-trinitrobenzyl chloride by reaction with an aqueous nitrogenous base providing hydroxide ion. The nitrogenous bases comprise ammonia and organic amines selected from primary, secondary and tertiary amines, such as alkyl amines, alkanolamines, and alkylene diamines. In general, nitrogenous bases having a $pK_B$ value between 3.20 and 4.80, preferably between 3.35 and 4.60, as measured in water at 25° C., provide a yield of HNS, which is greater than that obtained with the use of sodium hydroxide under otherwise similar reaction conditions. The reaction is conducted in a solvent comprising tetrahydrofuran and methanol, at ambient temperature, and in the complete absence of sodium hydroxide, the source of hydroxide ion recommended by Shipp and Kaplan for this reaction. The nitrogenous base is mixed with the benzyl chloride in a molar ratio of base to chloride of from 1.2:1 to 3.0:1, and preferably from 2.0:1 to 2.5:1.

The yields of HNS are dramatically increased and may be reliably obtained.

Accordingly, it is a principal object of the present invention to provide a method for the preparation of 2,2',4,4',6,6'-hexanitrostilbene (HNS) from the starting material of 2,4,6-trinitrobenzyl chloride.

It is a further object of the present invention to provide a method as aforesaid which results in higher yields of purified HNS.

It is a still further object of the present invention to provide a method as aforesaid which utilizes a nitrogenous base to provide hydroxide ions.

Other objects and advantages will become apparent to those skilled in the art from a review of the ensuing description.

DETAILED DESCRIPTION OF THE PREFERRED EMBODIMENT

The present invention comprises a process for the preparation of 2,2',4,4',6,6'-hexanitrostilbene (HNS) by the reaction of 2,4,6-trinitrobenzyl chloride with hydroxide ion provided by an aqueous solution of a nitrogenous base selected from ammonia and organic amines as noted above. Suitable amines include primary, secondary and tertiary amines, such as alkyl amines, cycloalkyl amines, alkylene diamines, and alkanolamines. Preferably, the amine is selected from the group consisting of a n-butylamine, isopropylamine, isobutylamine, triethylamine, cyclohexylamine, ethanolamine, and N,N-Diethylethanolamine. Of the foregoing amines, isopropylamine and triethylamine are most preferred and offer the highest yields, on the order of 70%, as measured after purification of the reaction product.

In general, the reaction conditions of the present process conform to those specified in the '413 patent and the article by Shipp and Kaplan. Accordingly, the trinitrobenzyl chloride is first dissolved in a mixture of tetrahydrofuran and methanol, and a quantity of an aqueous solution of the nitrogeneous base is added thereto. In accordance with the invention, the nitrogenous base and the benzyl chloride are combined in a molar ratio of base to chloride which ranges from 1.2:1 to 3.0:1, and preferably from 2.0:1 to 2.5:1. In the instance where isopropylamine is the nitrogenous base, the optimal ratio is 2.0:1.

The aqueous solution of the nitrogenous base is added to the trinitrobenzyl chloride solution with stirring, after which the resulting mixture is permitted to stand for 15 minutes. After this period of time, the solid reaction product that has precipitated is filtered off and washed with methanol. Subsequently, the product is washed with hot acetone to yield the purified HNS. Additional HNS may be obtained by evaporating the acetone extract and stirring the residue with acetone at ambient temperature, after which more HNS may be filtered off. This latter procedure may be repeated several times, and has been found to yield additional reaction product.

The present invention will be better understood from a consideration of the following examples.

Table 1 shows the variables of each of Examples 1-26, along with their corresponding results.

TABLE 1
YIELDS OF HNS FROM NITROGENOUS BASES AND TNBzCl (0.65 g.; 2.5 mmoles)

| Ex. # | Nitrogenous Base | Quantity of Base[a] Wt. (g.) | mmoles | Molar Ratio Base:TNBzCl[b] | HNS Yield (%) Crude | Acetone Washed |
|---|---|---|---|---|---|---|
| 1 | Ethanolamine | 0.18 | 3.0 | 1.20 | 61 | |
| 2 | | 0.30 | 4.9 | 1.96 | 65 | |
| 3 | | 0.36 | 5.9 | 2.36 | 69 | 64 |
| 4 | | 0.42 | 6.9 | 2.76 | 63 | |
| 5 | i-Propylamine | 0.23 | 3.9 | 1.56 | 71 | |
| 6 | | 0.29 | 4.9 | 1.96 | 75 | 69 |
| 7 | | 0.35 | 5.9 | 2.36 | 73 | |
| 8 | | 0.41 | 6.9 | 2.76 | 69 | |
| 9 | Triethylamine | 0.50[c] | 4.9 | 1.96 | 71 | |
| 10 | | 0.60[c] | 5.9 | 2.36 | 75 | 70 |
| 11 | | 0.69[c] | 6.9 | 2.76 | 71 | |
| 12 | N,N-Diisopropylethylamine | 0.76[d] | 5.9 | 2.36 | 27 | |
| 13 | Cyclohexylamine | 0.58 | 5.9 | 2.36 | 69 | 64 |
| 14 | n-Butylamine | 0.43 | 5.9 | 2.36 | 69 | 64 |
| 15 | i-Butylamine | 0.43 | 5.9 | 2.36 | 69 | 64 |
| 16 | N,N-Diethylethanolamine | 0.69 | 5.9 | 2.36 | 69 | 64 |
| 17 | Ammonia | 0.10 | 5.9 | 2.36 | 64 | 57 |
| 18 | Ethylamine | 0.27 | 5.9 | 2.36 | 63 | 58 |
| 19 | Diethylamine | 0.43 | 5.9 | 2.36 | 56 | 52 |
| 20 | Dimethylamine | 0.27 | 5.9 | 2.36 | 63 | 50 |
| 21 | Methylamine | 0.18 | 5.9 | 2.36 | 53 | 49 |
| 22 | Ethylenediamine | 0.35 | 5.9 | 2.36 | 55 | 51 |
| 23 | Piperidine | 0.50 | 5.9 | 2.36 | 41 | 36 |
| 24 | Morpholine | 0.51 | 5.9 | 2.36 | 43 | 39 |
| 25 | Triethanolamine | 0.88 | 5.9 | 2.36 | 10 | |
| 26 | Pyridine | 0.48 | 5.9 | 2.36 | 4 | |

NOTES:
[a] In 6 ml. of aqueous solution unless otherwise indicated (20 ml. stock solutions were prepared.)
[b] TNBzCl = 2,4,6-trinitrobenzyl chloride.
[c] The stock solution was prepared by first dissolving the amine in 4 ml. of methanol (except 5 ml. were required for 0.69 g.), then diluting to 25 ml. with water.
[d] The stock solution was prepared first dissolving the amine in 10 ml. of methanol, then diluting to 25 ml. with water.

EXAMPLE 1

0.65 grams corresponding to 2.5 mmoles of 2,4,6-trinitrobenzyl chloride were dissolved in 10 ml of tetrahydrofuran and 5 ml of methanol. To this resulting solution, 6 ml of an aqueous solution containing 0.18 g. of ethanolamine, corresponding to 3 mmoles, was added all at one time under brief agitation by stirring (several turns). The resulting solution was allowed to stand for 15 minutes, during which time the reaction product precipitated as a gold-to-pale gold to silvery solid. This solid was separated by filtration, washed with methanol, and thereafter washed with hot acetone, finally yielding the stilbene as a pale yellow solid, having a melting point of 315° (dec.). The acetone extract was then evaporated, and the solid residue was stirred with acetone at ambient temperature, whereupon more HNS was filtered off. This latter procedure was repeated in some of the examples that follow, yielding still greater amounts of the stilbene.

EXAMPLES 2-26

The procedure described in Example 1 was repeated except that the amount and type of base and the molar ratio of the base to the chloride, were varied, as indicated in Table 1 below.

Referring to Table 1, it is apparent that for the most part the alkyl amines, including the cycloalkyl amines, and the alkanol amines, performed favorably and produced higher yields of HNS than obtained using sodium hydroxide under similar conditions. Certain compounds, however, proved unfavorable, and are accordingly considered outside the scope of the invention. Specifically, Example 12, N,N-Diisopropylethylamine, and Examples 23 through 26 yielded results that were worse than the results obtainable by conventional processing with sodium hydroxide. It it therefore apparent from the foregoing that certain nitrogenous bases, and in particular, certain organic amines are contemplated within the scope of this invention and are capable of promoting the unexpectedly improved yields of HNS.

What we claim is:

1. The method for the prepartion of 2,2',4,4',6,6'-hexanitrostilbene which consists essentially of reacting 2,4,6-trinitrobenzyl chloride with hydroxide ion derived from a nitrogenous base having a $pK_B$ between 3.20 and 4.80 being dissolved in water.

2. The method of claim 1 wherein said nitrogenous base is selected from the group consisting of ammonia, alkyl amines, alkanolamines, alkylene diamines and cycloalkyl amines.

3. The method of claim 2 wherein said nitrogenous base is selected from the group consisting of ethylamine, triethylamine, isopropylamine, cyclohexylamine, n-butylamine, isobutylamine, N,N-diethylethanolamine, ethanolamine, ammonia, diethylamine, dimethylamine, methylamine, and ethylenediamine.

4. The method of claim 2 wherein said nitrogeneous base is selected from triethylamine and isopropylamine.

5. The method of claim 1 wherein said nitrogenous base is added as an aqueous solution.

6. The method of claim 1 wherein said trinitrobenzyl chloride and said nitrogenous base are present in a ratio with respect to each other ranging from 1.2:1 to 3.0:1.

7. The method of claim 6 wherein said ratio ranges from 2.0:1 to 2.5:1.

8. The method of claim 1 wherein said trinitrobenzyl chloride is first dissolved in a solution of tetrahydrofuran and methanol, and a quantity of an aqueous solution of said nitrogenous base is thereafter added thereto.

9. The method of claim 8 wherein said solution of trinitrobenzyl chloride and said aqueous solution of said notrogenous base are combined all at once under stirring, at ambient temperature, and the resulting mixture is permitted to stand 15 minutes, after which the precipitated reaction product comprising said hexanitrostilbene, may be filtered off.

10. The method of claim 9, further including recovering the precipitated hexanitrostilbene by filtration, washing the filtrate with methanol, and purifying the crude product by washing with hot acetone.

11. The method of claim 10, further comprising evaporating the washing solution utilized in said hot acetone washing step, mixing the residue of said evaporation with acetone at ambient temperature, and filtering off additional hexanitrostilbene.

12. The method of claim 11 wherein said evaporation, admixture with acetone, and subsequent filtering are conducted a plurality of times to obtain additional yield of said hexanitrostilbene.

* * * * *